United States Patent
Klein Nagelvoort et al.

(10) Patent No.: US 9,206,301 B2
(45) Date of Patent: *Dec. 8, 2015

(54) RESIN COMPOSITION SUITABLE FOR (RE)LINING OF TUBES, TANKS AND VESSELS

(71) Applicant: DSM IP ASSETS B.V., Heerlen (NL)

(72) Inventors: Joanna Klein Nagelvoort, Zwolle (NL); Cornelis Den Besten, Elburg (NL); Johan Franz Gradus Antonius Jansen, Geleen (NL)

(73) Assignee: DSM IP ASSETS B.V., Heerlen (NL)

( * ) Notice: Subject to any disclaimer, the term of this patent is extended or adjusted under 35 U.S.C. 154(b) by 82 days.

This patent is subject to a terminal disclaimer.

(21) Appl. No.: 13/891,172

(22) Filed: May 9, 2013

(65) Prior Publication Data

US 2013/0245177 A1  Sep. 19, 2013

Related U.S. Application Data

(63) Continuation of application No. 12/520,659, filed as application No. PCT/EP2007/011277 on Dec. 20, 2007, now Pat. No. 8,586,679.

(60) Provisional application No. 60/876,561, filed on Dec. 22, 2006.

(30) Foreign Application Priority Data

Dec. 22, 2006 (EP) ..................................... 06026727

(51) Int. Cl.
 *C08K 13/02* (2006.01)
 *C07C 69/01* (2006.01)
 *C07C 69/60* (2006.01)
 *C08G 59/17* (2006.01)
 *C09D 163/10* (2006.01)
 *C08K 5/13* (2006.01)
 *C08K 3/22* (2006.01)
 *C08K 5/103* (2006.01)

(52) U.S. Cl.
 CPC ............... *C08K 13/02* (2013.01); *C07C 69/01* (2013.01); *C07C 69/60* (2013.01); *C08G 59/1466* (2013.01); *C08K 5/13* (2013.01); *C09D 163/10* (2013.01); *C08K 3/22* (2013.01); *C08K 5/103* (2013.01); *Y10T 428/1352* (2015.01)

(58) Field of Classification Search
 None
 See application file for complete search history.

(56) References Cited

U.S. PATENT DOCUMENTS

| 5,985,456 | A | 11/1999 | Zhou et al. |
|---|---|---|---|
| 6,998,011 | B2 | 2/2006 | Schoenfeld et al. |
| 7,786,225 | B2 * | 8/2010 | Yasumura et al. ............. 525/530 |
| 8,586,679 | B2 * | 11/2013 | Klein Nagelvoort et al. 525/304 |
| 2012/0232228 | A1 | 9/2012 | Klein Nagelvoort et al. |

FOREIGN PATENT DOCUMENTS

| WO | 03/093381 | 11/2003 |
|---|---|---|
| WO | WO 03093381 A1 * | 11/2003 |
| WO | 2004/096878 | 11/2004 |
| WO | 2006/091446 | 8/2006 |

OTHER PUBLICATIONS

International Search Report for PCT/EP2007/011331 mailed May 6, 2008.

* cited by examiner

Primary Examiner — Satya Sastri
(74) Attorney, Agent, or Firm — Nixon & Vanderhye P.C.

(57) ABSTRACT

Structural, radically curable resin compositions suitable for (re)lining contain:
 a. 30-70 wt. % of a resin characterized by (i) a molecular weight $M_n$ between 500 and 3000 and (ii) an acid value between 0 and 30 mg KOH/g resin, and wherein at least 80% of the total amount of resin is vinyl ester resin,
 b. 30-70 wt. % of at least one reactive diluent, characterized in that at least 25% of the reactive diluent is a difunctional diluent having a molecular weight $M_n$ between 200 and 500 and the optional monofunctional diluent having a molecular weight $M_n$ between 100 and 200,
 c. 0.00001-5 wt. % initiator,
 d. 0.00001-5 wt. % inhibitor. wherein
the average molecular weight per reactive unsaturation (WPU) of the components (a) and (b) is equal or greater than 190 Dalton and that the amount of styrene in the resin composition is less than 5 wt. % (calculated as wt. % of the total weight of the components (a), (b), (c) and (d)).

19 Claims, No Drawings

RESIN COMPOSITION SUITABLE FOR (RE)LINING OF TUBES, TANKS AND VESSELS

This application is a continuation of commonly owned copending U.S. application Ser. No. 12/520,659, filed Oct. 19, 2009 (now U.S. Pat. No. 8,586,679), which is the national phase application of International Application PCT/EP2007/011277, filed Dec. 20, 2007, which designated the US and claims benefit of European Application No. 06026727.5, filed Dec. 22, 2006 and U.S. Provisional Application No. 60/876,561, filed Dec. 22,2006, the entire contents of each of which are hereby incorporated by reference.

The present invention relates to structural, radically curable resin composition suitable for (re)lining containing
(a) 30-70 wt. % of a resin,
(b) 30-70 wt. % of at least one reactive diluent,
(c) 0.00001-5 wt. % initiator,
(d) 0.00001-5 wt. % inhibitor,
wherein the amount of styrene in the resin composition is less than 5 wt. %. (the wt. % is relative to the total weight of the components (a), (b), (c) and (d)). The invention also relates to the use of such a resin composition in (re)lining, more in particular to the use of such a resin composition in flexible, sleeve-shaped objects for use in (re)lining. The invention further relates to a process for (re)lining a tube, tank or vessel with such a flexible, sleeve-shaped object.

As used herein, structural resin compositions are capable of providing structural parts. As meant herein, structural parts are considered to have a thickness of at least 0.5 mm and appropriate mechanical properties. Generally such resin compositions are non-aqueous systems. They contain at most 5% by weight of water.

As used herein, radically curable means that a network is formed via a radical polymerisation.

In the framework of the present invention, (re)lining is understood to be the provision on the inside of a hollow object or system, such as a pipe system (for example a sewage system, industrial line system or a transport line), a vessel, a tank or a house sewer connection and the like, of a layer with a thickness of at least 2 mm, but usually more than 3 mm and even up to 30-40 mm. The layer thickness of a (re)lining is generally chosen to be thicker as the diameter of the hollow object increases. The (re)lining generally has the object of contributing to the mechanical strength and ensuring the resistance of the hollow object or system to chemicals, corrosion, etc., as well as prevention of leaks. It should be noted that when a hollow object or system is for the first time provided with a lining on the inside, this is referred to as lining. Each subsequent time that a hollow object or system that is already internally lined is provided again with a lining, this is called relining. The (re)lining therefore refers to all situations where the lining is provided either for the first time or for any subsequent time.

(Re)linings are clearly distinguished from so-called coating applications, for which the layer thickness generally amounts to a maximum of 0.5 mm and for which entirely different requirements are specified for the surface of the layer (and for the adhesion to the substrate). As a rule a coating will, for example, have to meet high requirements regarding surface quality and drying (in particular when being cured to the air), but will not contribute to the mechanical strength.

A disadvantage of known resin compositions currently applied in (re)lining is the presence of considerable quantities of styrene, as a result of which styrene escapes, at least during the installation, and possibly residual styrene gradually escapes the first few days or weeks after laying such pipe systems, or even during the envisaged long-term use thereof, and causes an undesirable odour, and possibly even also toxic effects.

However, while the object at one hand is to create a formulation which differs from commercial resin composition applied in (re)lining in terms of styrene emissions, the application dictates that such a formulation must result in physical properties, at least chemical resistance, that are currently achieved with the commercial resin compositions.

Accordingly, the object of the present invention was to design a structural resin composition suitable for relining that show low or no emission of styrene while at the same time the radically curable resin composition having a viscosity similar to or even lower than that of currently employed styrenated resin compositions and the radically, cured resin composition must have similar or even better physical properties than those of radically cured, styrenated resin compositions. For example, at least the minimum requirements of typical norms for these types of products, like for example EN 13566-4, should be fulfilled.

It has surprisingly been found that this object can be achieved in that the structural, radically curable resin composition contains
a. 30-70 wt. % of resin, characterized by (i) a molecular weight $M_n$ between 500 and 3000 and (ii) an acid value between 0 and 30 mg KOH/g resin, and wherein at least 80% of the total amount of resin is vinyl ester resin and at most 20% of the total amount of resin is unsaturated polyester resin,
b. 30-70 wt. % of at least one reactive diluent, characterized in that at least 25% of the reactive diluent is a difunctional diluent having a molecular weight $M_n$ between 200 and 500 and the optional monofunctional diluent having a molecular weight $M_n$ between 100 and 200,
c. 0.00001-5 wt. % initiator,
d. 0.00001-5 wt. % inhibitor
further characterized in that the average molecular weight per reactive unsaturation (WPU) of the components (a) and (b) is equal or greater than 190 Dalton and that the amount of styrene in the resin composition is less than 5 wt. % (calculated as wt. % of the total weight of the components (a), (b), (c) and (d)).

Preferably, the resin composition contains 30-70 wt. % of vinyl ester resin characterized by (i) a molecular weight $M_n$ between 500 and 3000 and (ii) an acid value between 0 and 30 mg KOH/g resin; 30-70 wt. % of at least one reactive diluent, characterized in that at least 25% of the reactive diluent is a difunctional diluent having a molecular weight $M_n$ between 200 and 500 and the optional monofunctional diluent having a molecular weight $M_n$ between 100 and 200; 0.00001-5 wt. % initiator; and 0.00001-5 wt. % inhibitor, whereby the average molecular weight per reactive unsaturation (WPU) of the components (a) and (b) is equal or greater than 190 Dalton and the amount of styrene in the resin composition is less than 5 wt. % (calculated as wt. % of the total weight of the components (a), (b), (c) and (d)).

As used herein, the average molecular weight per reactive unsaturation (WPU) means the average molecular weight per reactive unsaturation present in the summed mass of the components containing reactive carbon-carbon unsaturations ((a)+(b)).

Preferably, the uncured resin composition has a viscosity between 300 and 1000 mPa·s (measured according to ISO 3219 at 23° C.), more preferably between 300 and 800 mPa·s and even more preferably between 400 and 700 mPa·s.

As used herein, a difunctional reactive diluent contains two reactive unsaturations, like for example two (meth)acrylate groups. A monofunctional reactive diluent contains one reactive unsaturation, like for example a (meth)acrylate group.

Preferably, at least 40% of the reactive diluent(s) is a difunctional diluent having a molecular weight $M_n$ between 200 and 500. Preferably, at least 25% and more preferably at least 40% of the reactive diluent(s) is a difunctional diluent having a molecular weight $M_n$ between 200 and 400. Suitable examples of difunctional reactive diluents having a molecular weight $M_n$ between 200 and 500 are PEG200 di(meth)acrylate, 1,4-butanediol di(meth)acrylate, 1,3-butanediol di(meth)acrylate, 2,3-butanedioldi(meth)acrylate, 1,6-hexanediol di(meth)acrylate and its isomers, diethyleneglycol di(meth)acrylate, triethyleneglycol di(meth)acrylate, glycerol di(meth)acrylate, trimethylolpropane di(meth)acrylate, neopentyl glycol di(meth)acrylate, dipropyleneglycol di(meth)acrylate, tripropyleneglycol di(meth)acrylate, PPG250 di(meth)acrylate, tricyclodecane dimethylol di(meth)acrylate, 1,10-decanediol di(meth)acrylate and/or tetraethylene glycol dimethacrylate. Preferred difunctional reactive diluents are 1,4-butanediol di(meth)acrylate, neopentylglycol di(meth)acrylate, PEG200 di(meth)acrylate, triethyleneglycol di(meth)acrylate and/or tripropylene glycol di(meth)acrylate.

Suitable examples of monofunctional reactive diluents having a molecular weight $M_n$ between 100 and 200 are hydroxylethyl (meth)acrylate, hydroxyl propyl (meth)acrylate, butyl (meth)acrylate, vinyl toluene, hexyl (meth)acrylate and cyclohexyl (meth)acrylate, alpha methyl styrene, tert. butyl styrene, phenoxyethyl (meth)acrylate, tetrahydro furfuryl (meth)acrylate and/or allyl (meth)acrylate. Preferred monofunctional reactive diluents are vinyl toluene, tetrahydro furfuryl (meth)acrylate, hydroxylethyl (meth)acrylate and/or hydroxylpropyl (meth)acrylate.

Preferably, the molecular weight of the resin is between 500 and 1500.

Preferably, the acid value of the resin composition is between 1 and 20 mg KOH/g resin.

At least 80% of the resin in the resin composition according to the invention is a vinyl ester resin or a mixture of vinyl ester resins. At most 20% of the total amount of the resin may be unsaturated polyester resin(s).

The vinyl ester resin as is comprised in the resin compositions according to the present invention and the unsaturated polyester resin as may be comprised in the resin compositions according to the invention may suitably be selected from the unsaturated polyester resins and vinyl ester resin as are known to the skilled person. Examples of suitable unsaturated polyester or vinyl ester resins to be used as basic resin systems in the resins of the present invention are, subdivided in the categories as classified by Malik et al., in J.M.S.-Rev. Macromol. Chem. Phys., C40(2&3), p. 139-165 (2000).

(1) Ortho-resins: these are based on phthalic anhydride, maleic anhydride, or fumaric acid and glycols, such as 1,2-propylene glycol, ethylene glycol, diethylene glycol, triethylene glycol, 1,3-propylene glycol, dipropylene glycol, tripropylene glycol, neopentyl glycol or hydrogenated bisphenol-A. Commonly the ones derived from 1,2-propylene glycol are used in combination with a reactive diluent such as styrene.

(2) Iso-resins: these are prepared from isophthalic acid, maleic anhydride or fumaric acid, and glycols. These resins may contain higher proportions of reactive diluent than the ortho resins.

(3) Bisphenol-A-fumarates: these are based on ethoxylated bisphenol-A and fumaric acid.

(4) Chlorendics: are resins prepared from chlorine/bromine containing anhydrides or phenols in the preparation of the UP resins.

(5) Vinyl ester resins: these are resins having unsaturated sites only in the terminal position. For example introduced by reaction of epoxy resins (e.g. diglycidyl ether of bisphenol-A, epoxies of the phenol-novolac type, or epoxies based on tetrabromobisphenol-A) with (meth)acrylic acid. Instead of (meth)acrylic acid also (meth)acrylamide may be used. The vinyl ester may also be a vinyl ester urethane which resins may be obtained by reacting a polyfunctional isocyanate with a polyhydric alcohol and/or a polyvalent amine and with a hydroxyalkyl (meth)acrylate. Examples are known from U.S. Pat. Nos. 3,297,745, 3,772,404, 4,618,658, GB-A-2217722, DE-A-3744390 and EP-A-534197. Preferably the vinyl ester urethane resin is a vinyl ester urethane dimethacrylate.

Besides these classes of resins also so-called dicyclopentadiene (DCPD) resins can be distinguished.

Preferably the resin is a vinyl ester resin or a mixture of vinyl ester resins. Preferred vinyl ester resins are epoxy vinyl ester resins or urethane vinyl ester resins, more preferred vinyl ester resins are epoxy vinyl ester resins.

The suitable quantity of (a) in the resin composition according to the invention lies between 30 and 70 wt. %. Preferably this quantity lies between 40 and 60 wt %.

Preferably, the resin composition according to the invention contains less than 2 wt % styrene, more preferably the resin composition is essentially styrene-free. Essentially free of styrene as used here means that the styrene concentration in the resin composition is lower than 0.01 wt % styrene.

The initiator (c), which is applied in the resin composition according to the invention, is as a rule chosen from initiators which are suitable for thermal curing and/or are suitable for curing by photo-initiation. Thermal curing is understood to be curing of the resin composition by means of heat. In case the resin composition is applied for relining, the heat is originating from heated water or gas used to pressurize the (re)lining. Photo-initiation is understood to be curing using irradiation with light of a suitable wavelength (photo irradiation). This is also referred to as light cure. In case of relining, the light energy is generally supplied via lamps placed or moved forward in the hollow objects.

The quantity of component (c) in the resin composition according to the invention as a rule lies between 0.00001-5 wt %. Preferably this quantity lies between 0.1 and 5 wt %.

In one embodiment of the invention, the initiator is a photo-initiator, preferably a cleavage type photo-initiator, more preferably a α-hydroxy aryl ketone like for instance Irgacure 184, Irgacure 369, Darocure 1173 (Ciba) or acyl phosphine oxides like for instance Lucerine TPO, Lucerine TPO-L (BASF), Irgacure 819 (Ciba) or mixtures thereof. Most preferably the photoinitiator is an acyl phosphine oxide. The acyl phosphine oxide is a mono acyl phosphine oxide or a bis acyl phosphine oxide. A preferred bis acyl phosphine oxide is bis(2,4,6-trimethylbenzoyl) phenylphosphine oxide (Irgacure 819). The quantity of photo-initiator is preferably between 0.1 and 2 wt. %, more preferably between 0.2 and 1 wt. %.

In another embodiment of the invention, the initiator is a thermal initiator. Examples of suitable thermal initiators are azo compounds like azo isobutyronitril (AIBN) and derivatives thereof, and organic peroxides. The thermal initiator is preferably an organic peroxide, or a combination of two or more organic peroxides.

Examples of suitable peroxides are, for instance, peroxy carbonates (of the formula —OC(O)O—), peroxyesters (of the formula —C(O)OO—), diacylperoxides (of the formula —C(O)OOC(O)—), dialkylperoxides (of the formula —OO—), etc. The peroxides can also be oligomeric or polymeric in nature. An extensive series of examples of suitable peroxides can be found, for instance, in US 2002/0091214-A1, paragraph [0018]. The skilled person can easily obtain information about the peroxides and the precautions to be taken in handling the peroxides in the instructions as given by the peroxide producers.

Examples of suitable organic peroxides are: tertiary alkyl hydroperoxides (such as, for instance, t-butyl hydroperoxide), other hydroperoxides (such as, for instance, cumene hydroperoxide), the special class of hydroperoxides formed by the group of ketone peroxides (perketones, being an addition product of hydrogen peroxide and a ketone, such as, for instance, methyl ethyl ketone peroxide and acetylacetone peroxide), peroxyesters or peracids (such as, for instance, t-butyl peresters, benzoyl peroxide, peracetates and perbenzoates, lauryl peroxide, including (di)peroxyesters),-perethers (such as, for instance, peroxy diethyl ether). Often the organic peroxides used as curing agent are tertiary peresters- or tertiary hydroperoxides, i.e. peroxy compounds having tertiary carbon atoms directly united to an —OO-acyl or —OOH group. Clearly also mixtures of these peroxides with other peroxides may be used in the context of the present invention. The peroxides may also be mixed peroxides, i.e. peroxides containing any two of different peroxygen-bearing moieties in one molecule). In case a solid peroxide is being used for the curing, the peroxide is preferably benzoyl peroxide (BPO) or peroxy carbonate peroxide.

Examples of suitable ketone peroxides are methyl-ethyl-ketone peroxide (MEKP), cyclohexanone peroxide, methyl-isobutyl-ketone peroxide, acetylacetone peroxide. Examples of suitable hydroperoxides are cumene hydroperoxide and tert butyl hydroperoxide.

The resin composition according to the invention containing a thermal initiator preferably further contains an accelerator, preferably a transition metal compound and/or organic compound. Examples of suitable transition metal compounds are Vanadium, Iron, manganese, copper, nickel, molybdenum, tungsten, cobalt, chromium compounds. The transition metal compound is preferably a cobalt compound or mixtures of cobalt compound with other metal salts. A suitable cobalt compound is for example cobalt octoate or cobalt naphthenate.

The organic compound can be any organic compound that can be oxidized or reduced. Suitable examples are 1,2-dioxo compounds, 1,3-dioxo compounds, thiols, and N containing compounds like amides and amines. Preferably the organic compound is an N-containing compound. Examples of N-containing compounds are dimethylaniline, diethylaniline, dimethylparatoluidine, diethylhydroxylamine, N,N-diethylacetoacetamide, benzyl amine, p-toluidine, 2-(N-ethylanilino)ethanol, triethanol amine, triethyl amine and Jeffamines, like for example Jeffamine D-2000.

The resin compositions according to the invention contain one or more inhibitors. The inhibitor (d) of the resin composition of the invention can be any radical inhibitor known to the skilled man, preferably chosen from the group of phenolic compounds, stable radicals like galvinoxyl and N-oxyl based compounds and/or phenothiazines. Suitable examples of inhibitors that can be used in the resin compositions according to the invention are, for instance, 2-methoxyphenol, 4-methoxyphenol, 2,6-di-t-butyl-4-methylphenol, 2,6-di-t-butylphenol, 2,4,6-trimethyl-phenol, 2,4,6-tris-dimethylaminomethyl phenol, 4,4'-thio-bis(3-methyl-6-t-butylphenol), 4,4'-isopropylidene diphenol, 2,4-di-t-butylphenol, 6,6'-di-t-butyl-2,2'-methylene di-p-cresol, hydroquinone, 2-methyl-hydroquinone, 2-t-butylhydroquinone, 2,5-di-t-butylhydroquinone, 2,6-di-t-butylhydroquinone, 2,6-dimethylhydroquinone, 2,3,5-trimethylhydroquinone, catechol, 4-t-butylcatechol, 4,6-di-t-butylcatechol, benzoquinone, 2,3,5,6-tetrachloro-1,4-benzoquinone, methylbenzoquinone, 2,6-dimethylbenzoquinone, napthoquinone, 1-oxyl-2,2,6,6-tetramethylpiperidine, 1-oxyl-2,2,6,6-tetramethylpiperidine-4-ol (a compound also referred to as TEMPOL), 1-oxyl-2,2,6,6-tetramethylpiperidine-4-one (a compound also referred to as TEMPON), 1-oxyl-2,2,6,6-tetramethyl-4-carboxyl-piperidine (a compound also referred to as 4-carboxy-TEMPO), 1-oxyl-2,2,5,5-tetramethylpyrrolidine, 1-oxyl-2,2,5,5-tetramethyl-3-carboxylpyrrolidine (also called 3-carboxy-PROXYL), aluminium-N-nitrosophenyl hydroxylamine, diethylhydroxylamine, phenothiazine and/or derivatives or combinations of any of these compounds.

Advantageously, the amount of inhibitor in the resin composition according to the invention is in the range of from 0.00001 to 5% by weight, preferably from 0.0001 to 2% by weight, more preferably, from 0.001 to 1% by weight. In case of thermal curing 2,6-di-t-butyl-4-methylphenol and 2-methylhydroquinone are very suitable inhibitors.

Preferably, the cured, unreinforced structural resin composition according to the invention has a tensile E-modulus (measured according to ISO 527-2) higher than 2000 MPa, preferably higher than 2500 MPa and more preferably higher than 3000 MPa. Preferably, the cured, unreinforced structural resin composition according to the invention has an elongation at break (measured according to ISO 527-2) higher than 2%. Preferably, the heat deflection temperature (HDT) (measured according to ISO 75-A) of the cured, unreinforced structural resin composition is higher than 80° C., more preferably higher than 90° C. and even more preferably higher than 100° C.

Preferably, the cured, unreinforced structural resin composition according to the invention has a tensile strength (measured according to ISO 527-2) higher than 40 MPa. Preferably, the shrinkage of the cured, unreinforced resin composition is less than 15%, preferably less than 10%. Preferably, the uncured resin composition has a flash point higher than 50° C.

As used herein, the term cured resin composition refers to a resin composition having reached the maximum cross-link density. This can quickly be assessed via an IR of the cured resin composition, especially the ATR technique is very suitable.

The inventors were surprisingly able to obtain a structural, radically curable resin compositions containing less than 5 wt. % styrene and even being essentially styrene free which resin composition has a viscosity between 300 and 1000 mPa·s (measured according to ISO 3219 at 23° C.) and even between 400 and 800 mPa·s while at the same time the cured, unreinforced resin composition have a tensile E-modulus (measured according to ISO 527-2) higher than 2000 MPa and even higher than 2500 MPa, an elongation at break (measured according to ISO 527-2) higher than 2%, a heat deflection temperature (measured according to ISO 75-A) higher than 80° C. and even higher than 90° C. The present invention therefore also relates to a structural, radically curable resin compositions containing 30-70 wt. % of an unsaturated polyester resin and/or vinyl ester resin, 30-70 wt. % of at least one reactive diluent, 0.00001-5 wt. % initiator, 0.00001-5 wt. % inhibitor and containing less than 5 wt. % styrene and even being essentially styrene free which resin composition has a viscosity between 300 and 1000 mPa·s (measured according to ISO 3219 at 23° C.) and even between 400 and 800 mPa·s while at the same time the cured, unreinforced resin composition have a tensile E-modulus (measured according to ISO 527-2) higher than 2000 MPa and even higher than 2500 MPa, an elongation at break (measured according to ISO 527-2) higher than 2%, a heat deflection temperature (measured according to ISO 75-A) higher than 80° C. and even higher than 90° C.

The resin composition according to the invention in addition optionally contains a filler in a weight ratio of 0.05:1 to 20:1, preferably in a weight ratio of 0.2:1 to 3:1, relative to the total weight of the components (a), (b), (c) and (d), the total of the weight percentages of the components (a), (b), (c) and (d) being 100. Suitable fillers are aluminium trihydrate, calcium carbonate, mica, microcrystalline silica, quartz powder, barite, fibres and/or talc. Examples of fibres are glass fibres and carbon fibres.

As used herein, pot life means the time period between adding the initiating system and the start of the radical polymerisation at 23° C. Shelf life on the other hand is the time in which the uninitiated resin composition remains stable. In case the initiator is a photo initiator, pot life is similar to shelf life as curing is only started by the external light trigger. In thermal curing systems, radical polymerisation is initiated after having added the thermal initiating system and the radical polymerisation and initiation are accelerated by raising the temperature. It is known that radical polymerisation can be retarded by adding inhibitors. It has now surprisingly been found that radical polymerisation at room temperature can be dramatically retarded and thus the pot life can be dramatically increased without affecting the polymerisation at increased temperature when the resin composition further contains a monomaleate and/or monofumarate compound. This effect is most pronounced in case a peroxide is part of the initiating system.

Preferably, the monomaleate and/or monofumarate compound is incorporated in the vinyl ester resin. Preferably, at least a part of the vinyl ester resin has been modified with maleic anhydride and/or fumaric acid, more preferably with maleic anhydride. Preferably, at least 0.5%, more preferably at least 1% of the vinyl ester resin has been modified with maleic anhydride and/or fumaric acid as increasing the amount of maleic anhydride and/or fumaric acid results in an increase of the pot life of the resin composition. Preferably, at most 20%, more preferably at most 10% of the vinyl ester resin has been modified with maleic anhydride and/or fumaric acid as further increasing the amount of maleic anhydride and/or fumaric acid results in a too high increase of the viscosity of the resin composition.

In a preferred embodiment, the modified vinyl ester is a vinyl ester with the following structure

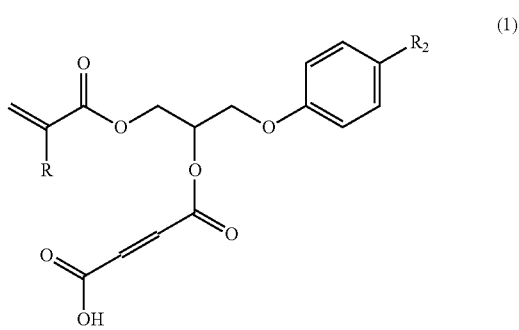

(1)

in which R=H or methyl and $R_2$=optionally substituted $C_1$-$C_{20}$ alkyl, optionally substituted $C_6$-$C_{20}$ aryl, part of a oligomeric or polymeric residue (>$C_{20}$), which can be optionally substituted.

Examples of substituents are, for instance, groups such as halogens, amines groups, alcohols, ethers, polyalkyleneoxy residues, carboxylates, anhydrides, amides, ureas, urethanes, etc. Examples of oligomeric or polymeric residues are, for instance, polyethylene, polypropylene, polystyrene, polyethylene oxides, polypropylene oxides, polycarbonates, polyurethanes, polyesters, etc. Very suitable polymeric residues are derived from epoxy resins or polyepoxides. Examples epoxy resins are for instance epoxy novolak resins and epoxy resins based on bisphenol A or Bisphenol F.

The modified vinyl ester resin can be prepared by first reacting a (meth)acrylic acid with a glycidyl ether or glycidyl ester followed by reacting the so obtained product with maleic anhydride and/or fumaric acid at a suitable temperature.

In a more preferred embodiment, the modified vinyl ester is a vinyl ester with the following structure (2)

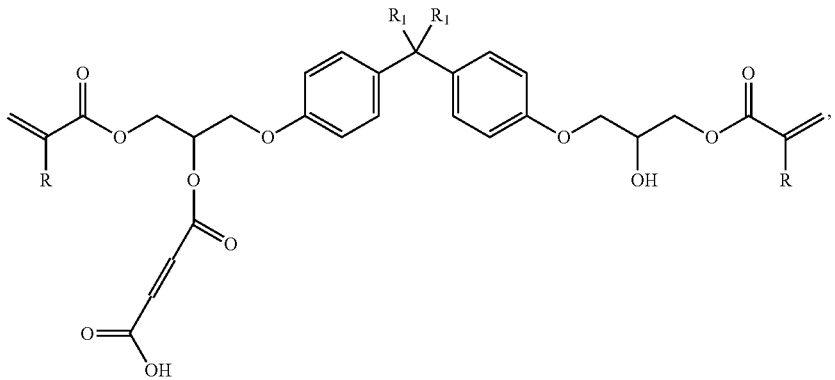

and/or with the following structure (3)

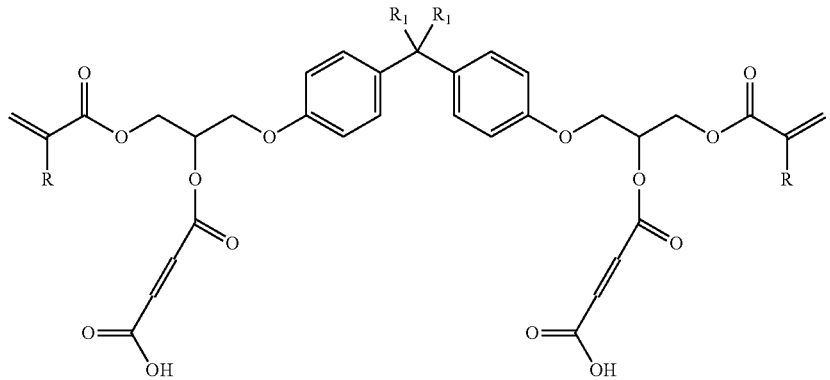

in which R is a denoted above and $R_1$ is H or a C1-C6 alkyl. Preferably $R_1$ is H or $R_1$ is methyl.

The invention also relates to the use of the resin composition according to the invention in a flexible, sleeve-shaped object for use in (re)lining. According to the invention the flexible, sleeve-shaped objects contain a supporting or reinforcing material that is impregnated with the structural, radically curable resin composition according to the invention, at least one of the surfaces of the sleeve-shaped object being provided with a barrier layer that is impermeable to the resin composition.

The supporting or reinforcing material of which the flexible, sleeve-shaped object consists is for example a fibrous web or needle felt of glass fibres, silica fibres, quartz fibres, carbon fibres, boron fibres, metal fibres, asbestos fibres, polyamide fibres (for example Kevlar® of Du Pont), polyester fibres, cotton fibres, silk fibres, polyethylene fibres and jute fibres. The person skilled in the art can readily determine the suitable fibres for a specific application or desired property of the structural element to be formed. Carbon fibres are used for example for applications in which a low weight and a high rigidity are desirable.

The barrier layer that is impermeable to the curable resin composition and that is provided at least one of the surfaces of the sleeve-shaped object is a layer of polyethylene, polypropylene, polyamide etc.

The present invention also provides for a method for (re)lining a tube, tank or vessel with a flexible, sleeve-shaped object as described above, where
(a) the flexible, sleeve-shaped object is introduced into a tube, tank or vessel, and then
(b) is pressurized therein with (i) a liquid or (ii) a gas, so that the flexible, sleeve-shaped object is forced against the inside of the wall of the tube, the tank or the vessel, and
(c) the curable resin composition present in the flexible, sleeve-shaped object is cured thermally in the case of (i) or (ii), or by photo-irradiation in the case of (ii).

The material from which a tube, tank or vessel itself is made can be chosen from a large series of suitable materials, for example cement, concrete, sandstone, GFK, polymer concrete, metal, steel, PVC, etc.

The present invention also relates to cured (re)liners for objects, in particular tubes, tanks or vessels, obtained by curing a resin composition according to the invention. In case the resin composition comprises a thermal initiator, the curing is effected using thermal curing. In case the resin composition comprises a photo-inititiator, the curing is effected using photo curing.

The present invention further relates to compounds according to structure 1

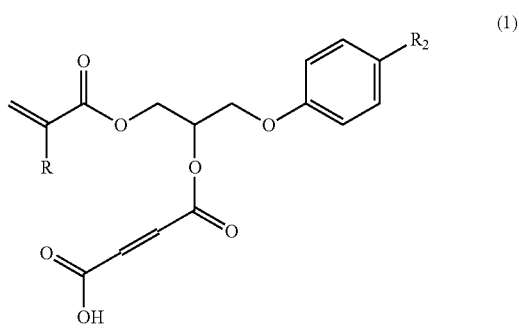

in which R=H or methyl and $R_2$=optionally substituted $C_1$-$C_{20}$ alkyl, optionally substituted $C_6$-$C_{20}$ aryl, part of a oligomeric or polymeric residue (>$C_{20}$), which can be optionally substituted.

Examples of substituents are, for instance, groups such as halogens, amines groups, alcohols, ethers, polyalkyleneoxy residues, carboxylates, anhydrides, amides, ureas, urethanes, etc. Examples of oligomeric or polymeric residues are, for instance, polyethylene, polypropylene, polystyrene, polyethylene oxides, polypropylene oxides, polycarbonates, polyurethanes, polyesters, etc. Very suitable polymeric residues are derived from epoxy resins or polyepoxides. Examples epoxy resins are for instance epoxy novolak resins and epoxy resins based on bisphenol A or Bisphenol F.

In a preferred embodiment, the compound is a modified vinyl ester with the following structure (2)

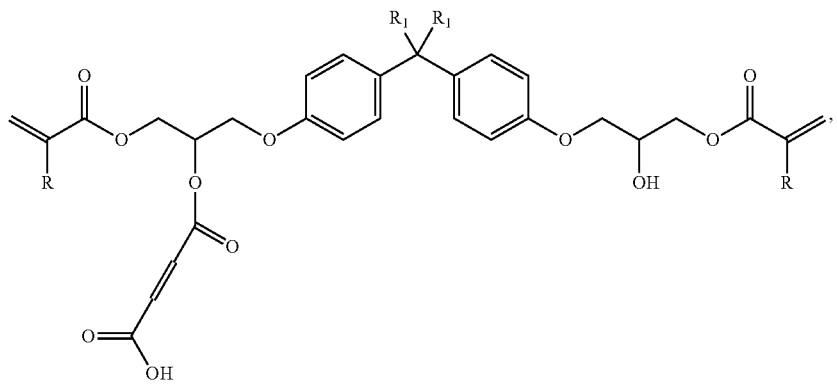

and/or with the following structure (3)

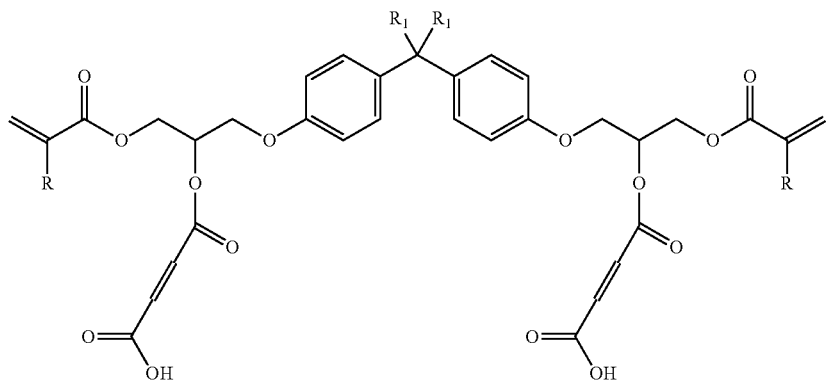

in which R is a denoted above and $R_1$ is H or a C1-C6 alkyl. Preferably $R_1$ is H or $R_1$ is methyl.

The present invention also relates to a method for preparing such compounds by first reacting a (meth)acrylic acid with a glycidyl ether or glycidyl ester followed by reacting the so obtained product with maleic anhydride and/or fumaric acid at a suitable temperature.

The present invention also relates to a resin composition containing compounds with structure (1). The resin composition preferably further contains a reactive diluent, an inhibitor and a radical initiator as defined herein above.

Finally, the present invention relates to the use of resin composition containing compounds having structure (1) or having structure (2) and/or (3) in various applications such as for instance chemical anchoring, roofing, relining, gel coats, containers, tanks, pipes, automotive parts, flooring, windmill blades, aviation, off shore applications.

The invention will now be elucidated further on the basis of a few examples, without however being limited to the compositions shown in the examples and comparative experiments.

The test method for tensile testing (tensile strength, E-modulus, elongation at break) is according to ISO 527-2 and for HDT according to ISO 75-A. The test method for viscosity measurement is according to ISO 3219.

Synthesis of Resins
Resin Mixture A 362 g epoxy resin with average mol mass of 350 is heated up to 100° C., continuously stirring using oxygen sparge and nitrogen blanket. At this temperature, 40 g of methacrylic acid, 0.1 g chromium chloride and 0.08 g hydrochinon are added. After 15 minutes everytime 3×40 g of methacrylic acid is added. Reaction is maintained and synthesis is ended at an acid number <5 mg KOH/g and EEW (epoxy equivalent weight of 5000-8000 g/epoxy. After reaching the end point the resin (having a WPU of 280); hereinafter referred to as resin A) is cooled down and dissolved in 95 g 1,4-butanediol dimethacrylate (BDDMA). Resin mixture A thus contains 15 wt % BDDMA.

Resin Mixture B 425 g epoxy resin with average mol mass of 350 and 82 g diphenylol propane and 0.8 g triphenyl phosphine are heated up to 110° C. After reaching exotherm, reaction is maintained at 115° C. until EEW (epoxy equivalent weight is <300 g/epoxy). After that mixture is cooled down to 110° C., 0.3 g 2,6 di-tert-butyl-p-cresol is added followed by 126 g methacrylic acid (dosing time 1 hr). After dosing 10% of methacrylic acid, 0.9 g dimethylbenzyl amine is added. Reaction is maintained until viscosity is 400-480 mPa·s (Cone & Plate at 125° C.) and acid number is 10-16 mg KOH/g. Finally when spec has reached, 0.2 g hydrochinon is added and resin B (having a WPU of 432) is cooled down to 80° C. and dissolved in 309 g 1,4-butanediol dimethacrylate. Resin mixture A thus contains 33 wt % BDDMA.

Resin C

Monomer-free unsaturated mixed resin, liquid at room temperature.

This mixed resin was obtained by heating 938 g polypropylene glycol bisphenol A, 89 g fumaric acid and 0.12 g hydroquinone within 2 hours to 210° C. with continuous stirring in a standard polycondensation reactor, use being made of a vacuum (to max. 0.1 bar): start of vacuum 1 hour after reaching 210° C. The synthesis is ended at an acid number of <20 mg KOH/g and a viscosity at 23° C. of <4 dPa·s. The resin has a WPU of 1338.

Resin Mixture D

Resin D is synthesized in the same way as resin A but before dissolving in 1,4-BDDMA, 15.6 g maleic anhydride is added. After reaction time of 3 hrs, resin D (having a WPU of 269) is cooled down and dissolved in 98 g 1,4-butanediol dimethacrylate. Finally, 0.03 g 2,6 di-tert-butyl-p-cresol is added. Resin mixture D thus contains 15 wt % BDDMA.

EXAMPLES 1-4 AND COMPARATIVE EXPERIMENTS A-C

Formulations were prepared according to table 1 (amounts given are wt. %). The components were mixed at room temperature. The viscosities and acid values of the formulations were determined. Next the resins were cured at room temperature using 0.2% of a 10% solution of cobalt octoate, 1.0% of a 10% solution of dimethyl aniline and 2.0% methylethylketon peroxide (Butanox M50) followed by a postcure of 24 hours at 60° C. and 24 hours at 80° C. after which the mechanical properties were determined. The following abbreviations are used:

PEG200DMA=polyethyleneglycol dimethacrylate (molecular weight $M_n$ 330)

1,4-BDDMA=1,4-butanediol dimethacrylate (molecular weight $M_n$ 226)

HPMA=hydroxypropylmethacrylate (molecular weight $M_n$ 144)

TABLE 1

| Resin mixtures (in wt. %) | Example 1 | Example 2 | Example 3 | Example 4 | Comp exp A | Comp exp B | Comp exp C |
|---|---|---|---|---|---|---|---|
| Resin A | 59 | | 65 | | | 59 | 71 |
| Resin B | | 67 | | | 74 | | |
| Resin C | 5 | | | | | 10 | |
| Resin D | | | | 65 | | | |
| PEG200DMA | 35 | | 35 | 35 | | | |
| 1,4 BDDMA | 1 | | | | 26 | 31 | 20 |
| HPMA | | 33 | | | | | |
| IDMA | | | | | | | 9 |
| Viscosity, 23° C. (mPa · s) | 602 | 433 | 576 | 695 | 1056 | 856 | 528 |
| Acid value (mgKOH/g) | 1.1 | 5.2 | 1.2 | 10.1 | 5.8 | 2.1 | 1.3 |
| WPU | 207 | 190 | 201 | 198 | 180 | 185 | 189 |
| Tensile Strength [MPa] | 60 | 67 | 64 | 70 | 45 | 48 | 38 |
| E-mod [MPa] | 2976 | 3606 | 3200 | 3372 | 3158 | 3600 | 2187 |
| El at break [%] | 2.8 | 2.1 | 2.6 | 2.7 | 1.5 | 1.5 | 2.3 |
| HDT [° C.] | 98 | 90 | 104 | 118 | 100 | 189 | 70 |

These examples and comparative examples show that only with resin formulations according to the invention the mechanical properties required for relining can be achieved. For instance only with WPU's>190 the required mechanical properties like for example elongation at break, HDT and tensile strength can be achieved (examples 1-4 vs comparative experiments A-C).

EXAMPLES 5-6

Mechanical Properties of Filled Systems

Of (re)lining laminates (6 mm thickness), with as the supporting material polyester needle felt, mechanical properties were measured after curing 6 hrs at 80° C. between 2 metal heating plates, the mechanical properties are stated in Table 2. This table also gives the ISO standards of the test methods used for the determination of the mechanical properties of the (re)lining laminate.

The laminates were produced as follows: First 20% of the indicated resin mixture amount was mixed with fumed silica using high shear mixer (dissolver blades) to mix in the fumed silica properly. After that the resulting amount of resin was mixed in at lower shear until homogeneous mixture was obtained. This was followed by addition of filler and cobalt octoate solutions. Finally, pre-mix of peroxides were added. By means of hand lay-up, after making the mixture free of air by means of vacuum, polyester needle felt was impregnated. Impregnated felt material was placed between two metal plates and thickness was fixed with distance blocks. Eventual excess of resin was squeezed out. Curing was started by increasing the temperature of the metal plates to 80° C.

TABLE 2

| | | Example 5 | Example 6 |
|---|---|---|---|
| Composition (in wt. %) | | Laminate A | Laminate B |
| Resin mixture example 3 | | 99 | |
| Resin mixture example 4 | | | 99 |
| Fumed silica | | 1 | 1 |
| Al$_2$(OH)$_3$ filler | | 40 | 40 |
| Bis (4-tert-butylcyclohexyl)peroxydicarbonate | | 0.8 | 0.8 |
| Tert butyl perbenzoate | | 1.0 | 1.0 |
| Cobalt octoate (1% solution) | | 1.0 | 1.0 |
| Polyester needle felt | | 14 | 14 |
| Flexural strength [MPa] | ISO 178 | 40 | 56 |
| E-modulus [MPa] | ISO 178 | 3800 | 4679 |
| Outer fibre strain [%] | ISO 178 | 1.1 | 4.7 |

Examples 5 and 6 clearly show that the resin compositions according to the invention are suitable for relining. Furthermore, these examples demonstrate that using maleic acid modified vinyl ester resin (example 6) further significantly improves the mechanical properties compared to using a vinyl ester resin that has not been modified with maleic acid (example 5). For example, the E-modulus in example 6 is 23% higher than in example 5, while the E-modulus of the cured, unfilled resin composition in example 4 (using a maleic acid modified vinyl ester resin) is only 5% higher than in example 3 (using a vinyl ester resin that has not been modified with maleic acid).

EXAMPLES 7-14

Pot Life and Cure Measurements
Curing

The resin mixtures of example 3 resp. 4 were cured at 60° C. with the addition of 0.8% bis(4-tert-butylcyclohexyl) peroxydicarbonate together with 1.0% tert butyl perbenzoate and 1.0% of a 1% solution of cobalt octoate in an aliphatic ester (accelerator NL-49-P (AKZO Nobel). The curing properties are stated in Table 3. The test was performed by measuring the physical gel time and separately the peak time and exotherm using a 13 mm internal diameter test tube (length 15 cm) directly placed in a water bath at described temperature. Peak time and temperature were measured using 1.5 mm thick thermocouple, measuring in the centre of the resin mass.
Pot Life Pot life was measured according the following method: using the same mixing sequence as described for the mechanical properties, after addition of the peroxides eventually extra 2,6 di-tert-butyl-p-cresol is added, 400 g of resin mixture (either with or without filler) is stored in glass jars of 720 ml. These jars are placed directly in a water bath conditioned at 23° C. Three times a day is checked whether resin mixture is still liquid. The moment the mixture starts to gel is defined as the pot life (in hrs/days) of the formulation.

late (re)lining laminates, impregnated with a mixture of resin mixture D and photoinitiators, mechanical properties were measured after curing using UVA spot 400G of Dr. Hönle as UV lamp having an output of 900 mW/cm$^2$ (output determined at a distance of 20 cm from the UVA spot). The mechanical properties are stated in Table 4. The laminates were produced as follows: After making the mixture free of air by means of vacuum, glass mats of Vetrotex M123 CSM were impregnated by means of hand lay-up and covered with foil. The UV lamp was prestarted before the actual curing took place and the laminate was placed on a cooling plate.

TABLE 4

|  | Example 15 |
|---|---|
| Composition (in wt. %) | Laminate C |
| Resin mixture D | 99 |
| Fumed silica | 1 |
| Lucirin TPO (photo-initiator BASF) | 0.23 |
| Irgacure 651 (photo-initiator Ciba) | 0.07 |
| Vetrotex M123 CSM glass mat | 33 |
| Flexural strength [MPa]   ISO 178 | 190 ± 5 |
| E-modulus [MPa]   ISO 178 | 7760 ± 400 |

The invention claimed is:

1. A structural, radically curable resin composition suitable for (re)lining comprising:
   (a) 30-70 wt.% of resin having (i) a molecular weight Mn between 500 and 3000 and (ii) an acid value between 0 and 30 mg KOH/g resin, and wherein at least 80% of the total amount of resin is vinyl ester resin,
   (b) 30-70 wt.% of at least one reactive diluent, wherein at least 25% of the reactive diluent is a difunctional diluent having a molecular weight Mn between 200 and 500 and an optional monofunctional diluent having a molecular weight Mn between 100 and 200, (c) 0.00001-5 wt.% of an initiator, and
   (d) 0.00001-5 wt.% of an inhibitor, wherein the average molecular weight per reactive unsaturation (WPU) of the components (a) and (b) is equal to or greater than 190 Dalton and that the amount of styrene in the resin composition is less than 5 wt.% based on the total weight of the components (a), (b), (c) and (d), and wherein

TABLE 3

| Composition (in wt. %) | Ex. 7 | Ex. 8 | Ex. 9 | Ex. 10 | Ex. 11 | Ex. 12 | Ex. 13 | Ex. 14 |
|---|---|---|---|---|---|---|---|---|
| Resin mixture example 3 | 99 | 99 | 99 | 99 | | | | |
| Resin mixture example 4 | | | | | 99 | 99 | 99 | 99 |
| Fumed silica | 1 | 1 | 1 | 1 | 1 | 1 | 1 | 1 |
| Al$_2$(OH)$_3$ filler | | 40 | | 40 | | 40 | | 40 |
| Bis(4-tert-butylcyclohexyl)peroxydicarbonate | 0.8 | 0.8 | 0.8 | 0.8 | 0.8 | 0.8 | 0.8 | 0.8 |
| Tert butyl perbenzoate | 1.0 | 1.0 | 1.0 | 1.0 | 1.0 | 1.0 | 1.0 | 1.0 |
| Cobalt octoate (1% solution) | 1.0 | 1.0 | 1.0 | 1.0 | 1.0 | 1.0 | 1.0 | 1.0 |
| 2,6 di-tert-butyl-p-cresol (10% solution in ethanol) | | | 0.1 | 0.1 | | | 0.1 | 0.1 |
| Gel time, 60° C. (minutes) | 8.0 | | | | 9.9 | | 17.2 | |
| Peak time, 60° C. (minutes) | 17.4 | | | | 25.2 | | 36.4 | |
| Exotherm (° C.) | 156 | | | | 139 | | 112 | |
| Pot life, 23° C. (hrs) | 8 | <2 | <12 | <16 | 48 | 60 | 192 | >200 |

These examples clearly demonstrate that by maleic acid modified vinyl ester resin using the pot life can be prolonged dramatically. Comparing examples 9-10 with examples 13-14 further shows that adding inhibitor to a resin mixture containing maleic acid modified vinyl ester resin results in a remarkebly increase of pot life while adding inhibitor to a resin mixture not containing maleic acid modified vinyl ester resin does not result in such a remarkebly increase of pot life.

EXAMPLE 15

Mechanical Properties of UV Cured Resin Systems

Of laminates (4.7 mm total thickness) containing 5 layers of a fibrous web of Vetrotex M123 CSM glass fibres to simuthe resin composition further comprises a monomaleate and/or monofumarate compound.

2. The structural resin composition according to claim 1, wherein the resin composition has a viscosity between 300 and 1000 mPa.s as measured according to ISO 3219 at 23° C.

3. The structural resin composition according to claim 1, wherein at least 40% of the reactive diluent is a difunctional diluent having a molecular weight Mn between 200 and 500.

4. The structural resin composition according to claim 1, wherein the difunctional diluent has a molecular weight Mn between 200 and 400.

5. The structural resin composition according to claim 1, wherein the difunctional diluent is selected from the group consisting of 1,4-butanediol di(meth)acrylate, neopentylglycol di(meth)acrylate, PEG200 di(meth)acrylate, triethylene glycol di(meth)acrylate and tripropylene glycol di(meth)acrylate.

6. The structural resin composition according to claim 1, wherein the monofunctional diluent is selected from the group consisting of vinyl toluene, tetrahydro furfuryl (meth)acrylate, hydroxyl ethyl (meth)acrylate and hydroxyl propyl (meth)acrylate.

7. The structural resin composition according to claim 1, wherein the molecular weight of the resin is between 500 and 1500.

8. The structural resin composition according to claim 1, wherein the resin is a vinyl ester resin or a mixture of vinyl ester resins.

9. The structural resin composition according to claim 1, wherein the resin is an epoxy vinyl ester resin.

10. The structural resin composition according to claim 1, wherein the resin composition contains less than 2 wt.% styrene.

11. The structural resin composition according to claim 1, wherein the resin composition is essentially styrene free.

12. The structural resin composition according to claim 1, wherein the initiator is a photo-initiator or a thermal initiator.

13. The structural resin composition according to claim 1, wherein the resin composition also contains a filler in a weight ratio of 0.05:1 to 20:1, relative to the total weight of the components (a), (b), (c) and (d), the total of the weight percentages of the components (a), (b), (c) and (d) being 100.

14. The structural resin composition according to claim 13, wherein the composition comprises a filler in a weight ratio of 0.2:1 to 3:1.

15. The structural resin composition according to claim 13, wherein the filler is selected from the group consisting of aluminium trihydrate, calcium carbonate, mica, microcrystalline silica, quartz powder, barite, fibres and talc.

16. A structural, radically curable resin composition suitable for (re)lining comprising:
   (a) 30-70 wt.% of resin having (i) a molecular weight Mn between 500 and 3000 and (ii) an acid value between 0 and 30 mg KOH/g resin, and wherein at least 80% of the total amount of resin is vinyl ester resin,
   (b) 30-70 wt.% of at least one reactive diluent, wherein at least 25% of the reactive diluent is a difunctional diluent having a molecular weight Mn between 200 and 500 and an optional monofunctional diluent having a molecular weight Mn between 100 and 200,
   (c) 0.00001-5 wt.% of an initiator, and
   (d) 0.00001-5 wt.% of an inhibitor, wherein
   the average molecular weight per reactive unsaturation (WPU) of the components (a) and (b) is equal to or greater than 190 Dalton and that the amount of styrene in the resin composition is less than 5 wt.% based on the total weight of the components (a), (b), (c) and (d), and wherein
   at least a part of the vinyl ester resin has been modified with maleic anhydride and/or fumaric acid.

17. The structural resin composition according to claim 16, wherein at least part of the vinyl ester resin has been modified with maleic anhydride and fumaric acid.

18. The structural resin composition according to claim 16, wherein the modified vinyl ester is a vinyl ester with the following structure (2):

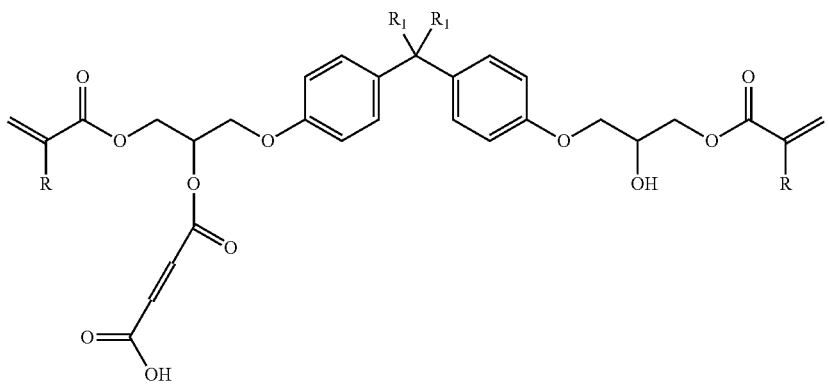

and/or with the following structure (3):

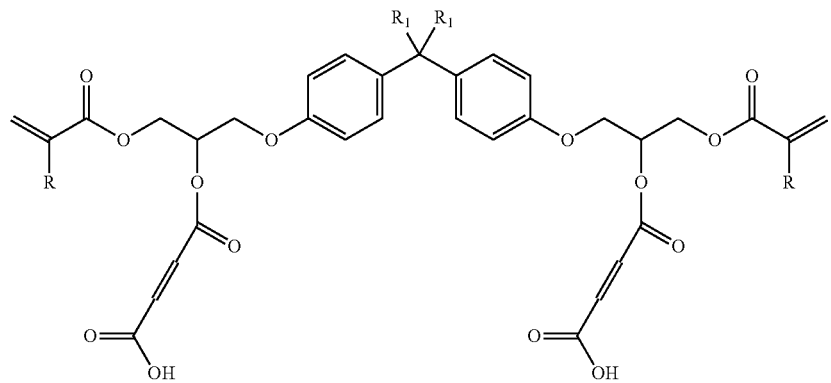

in which R = H or methyl and $R_1$ is H or a $C_1$-$C_6$ alkyl.

19. A structural, radically curable resin composition suitable for (re)lining comprising:
  (a) 30-70 wt.% of resin having (i) a molecular weight Mn between 500 and 3000 and (ii) an acid value between 0 and 30 mg KOH/g resin, and wherein at least 80% of the total amount of resin is vinyl ester resin,
  (b) 30-70 wt.% of at least one reactive diluent, wherein at least 25% of the reactive diluent is a difunctional diluent having a molecular weight Mn between 200 and 500 and an optional monofunctional diluent having a molecular weight Mn between 100 and 200,
  (c) 0.00001-5 wt.% of an initiator, and
  (d) 0.00001-5 wt.% of an inhibitor, wherein
  the average molecular weight per reactive unsaturation (WPU) of the components (a) and (b) is equal to or greater than 190 Dalton and that the amount of styrene in the resin composition is less than 5 wt.% based on the total weight of the components (a), (b), (c) and (d), and wherein
  at least part of the vinyl ester resin has been modified with maleic anhydride.

* * * * *